United States Patent [19]
Johnson

[11] Patent Number: 5,571,195
[45] Date of Patent: Nov. 5, 1996

[54] PROTHESIS FOR AN ARTIFICIAL JOINT HAVING A WEAR PARTICLE COLLECTION CAPABILITY

[76] Inventor: Lanny L. Johnson, 4528 Hagadorn, East Lansing, Mich. 48823

[21] Appl. No.: 453,877

[22] Filed: May 30, 1995

[51] Int. Cl.$^6$ ................................. A61F 2/30; A61F 2/34
[52] U.S. Cl. ................................. 623/18; 623/20; 623/23
[58] Field of Search ................................. 623/16, 17, 18, 623/19, 20, 21, 22, 23, 66

[56] References Cited

U.S. PATENT DOCUMENTS

| | | | |
|---|---|---|---|
| 3,648,294 | 3/1972 | Shahrestani | 623/18 |
| 3,924,275 | 12/1975 | Heimke et al. | 623/23 |
| 4,024,588 | 5/1977 | Janssen et al. | 623/18 |
| 4,032,994 | 7/1977 | Frey | 623/22 |
| 4,731,088 | 3/1988 | Collier | 623/18 |
| 5,021,063 | 6/1991 | Tager | 623/22 |
| 5,133,767 | 7/1992 | Frey et al. | 623/23 |
| 5,171,289 | 12/1992 | Tornier | 623/23 |
| 5,171,327 | 12/1992 | Koch et al. | 623/18 |
| 5,316,550 | 5/1994 | Fontz | 623/23 |
| 5,340,362 | 8/1994 | Carbone | 623/23 |
| 5,489,308 | 2/1996 | Kuslich et al. | 623/17 |

FOREIGN PATENT DOCUMENTS 3306171  12/1983  Germany ........................ 623/23

*Primary Examiner*—David Isabella
*Attorney, Agent, or Firm*—Cushman Darby & Cushman, L.L.P.

[57] ABSTRACT

A prosthesis for an artificial joint is provided with an interior passage which communicates with the joint area so that fluid from the joint circulates through the passage. Wear particles carried by fluid are deposited by gravity within the passage. Alternatively, a particle collecting filter is positioned in the passage, or in the case of a prosthesis formed from a magnetizable metal, a portion of the passage wall is magnetized to collect metal wear particles.

4 Claims, 1 Drawing Sheet

PROTHESIS FOR AN ARTIFICIAL JOINT HAVING A WEAR PARTICLE COLLECTION CAPABILITY

BACKGROUND OF THE INVENTION

A significant problem encountered in present day artificial joints is the creation of wear particles which cause inflammation, cyst formation and joint loosening. Such problems heretofore have only been resolved by resorting to additional surgery.

SUMMARY OF THE INVENTION

The present invention has as its objective a prosthesis feature which permits wear particles created during the use of artificial joints to be displaced from the joint area. This is accomplished by providing in the prosthesis itself one or more relief passages through which joint fluids can circulate. The passages are designed such that wear particles carried by the fluid are deposited within the prosthesis itself at a location where the particles cannot cause inflammation, cyst formation or joint loosening. Alternatively, in a preferred embodiment of the invention, means are provided at accessible sites in the passages for collecting the particles so that by percutaneous access to the site, a needle, under x-ray image control, can withdraw the collected particles.

BRIEF DESCRIPTION OF THE DRAWING

The invention now will be described in greater detail by reference to the accompanying drawing, FIG. 1, an elevational view illustrating a conventional hip prosthesis which has been modified to incorporate the invention.

DESCRIPTIONS OF THE PREFERRED EMBODIMENTS

Figure 1:
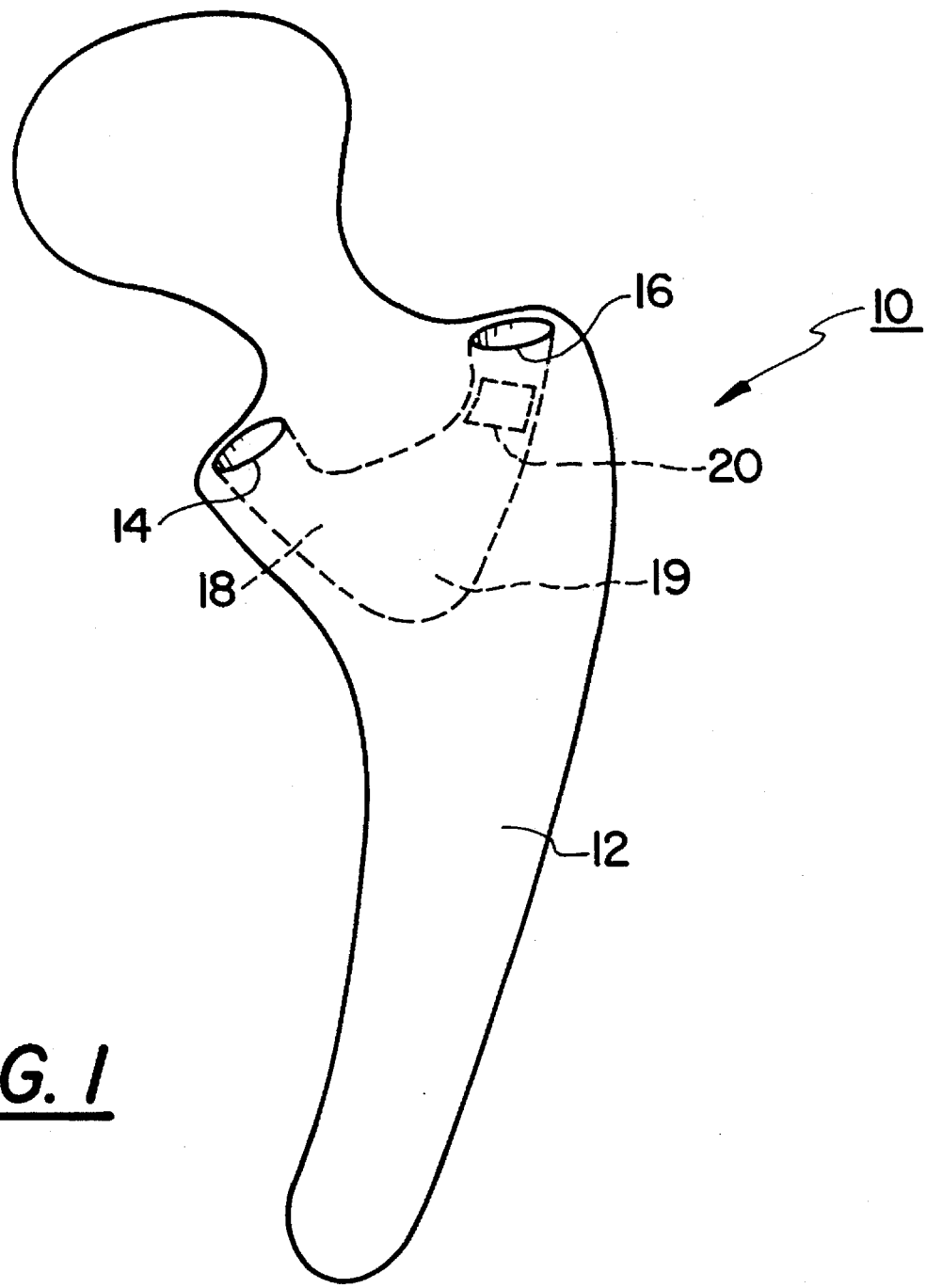

Although a hip prosthesis is utilized in describing the invention, it will be understood that the same features employed for collecting wear particles in such a prosthesis can be incorporated in other artificial joints such as those used in knee, shoulder, elbow and ankle surgery, or the like.

Referring to FIG. 1, a conventional hip prosthesis 10 is provided in the proximal portion of its femoral stem 12 with openings 14 and 16 which communicate to form a passage 18 having a particle-receiving chamber 19. The openings are located such that with the prosthesis positioned within the body, joint fluid can enter the holes and circulate through the passage. The orientation of the openings is such that as wear particles are created in the joint, they are carried through the passage and are deposited, by gravity, at the lowermost portion of the chamber 19. Periodically, under x-ray image control, a needle can be inserted within an opening so as to withdraw particles which have been so deposited in the chamber.

To further facilitate collection of wear particles, the passage can be provided with a filter material 20 at a convenient location. Alternatively, in the case of a magnetizable metal prosthesis, a selected area of the passage can be magnetized to provide a collection site for particles separated from the prosthesis through wear. The invention also contemplates the use of a chemical material within the passage having an affinity for the wear particles so as to collect them within the chamber 19.

It will be understood that the channel openings formed in various prostheses can be provided at any convenient location so long as they are accessible to the source of the wear particles.

What is claimed is:

1. A synovial joint prosthesis, said prosthesis having openings on an exterior surface thereof and being provided with an interior passage extending between said openings, said openings and interior passage being oriented to cause unassisted natural circulation of synovial joint fluid through the passage and to permit particles carried by said fluid to be deposited within the passage in the prosthesis.

2. A synovial joint prosthesis, said prosthesis having openings on an exterior surface thereof and being provided with an interior passage extending between said openings, said openings and interior passage being oriented to cause unassisted natural circulation of synovial joint fluid through the passage; and means provided within the passage for collecting particles carried by said fluid.

3. A prosthesis as set forth in claim 2, wherein said prosthesis is formed from a magnetizable metal and wherein said particle collecting means includes a magnetized portion of said prosthesis along said passage.

4. A synovial joint prosthesis, said prosthesis having openings on an exterior surface thereof and being provided with an interior passage extending between said openings, said openings and interior passage being oriented to cause natural circulation of synovial joint fluid through the passage; and a filter located within the passage for collecting particles carried by said fluid.

\* \* \* \* \*